(12) United States Patent
Kataishi et al.

(10) Patent No.: US 7,250,042 B2
(45) Date of Patent: Jul. 31, 2007

(54) THROMBUS SUCTION CATHETER WITH IMPROVED SUCTION AND CROSSING

(75) Inventors: Yuichi Kataishi, Yokohama (JP); Satoru Mori, Osaka (JP); Yoshihiko Sano, Osaka (JP); Toshihiro Kikuchi, Osaka (JP); Takaaki Isshiki, Tokyo (JP)

(73) Assignee: Nipro Corporation, Osaka (JP)

( * ) Notice: Subject to any disclaimer, the term of this patent is extended or adjusted under 35 U.S.C. 154(b) by 261 days.

(21) Appl. No.: 10/761,806

(22) Filed: Jan. 22, 2004

(65) Prior Publication Data

US 2005/0015073 A1    Jan. 20, 2005

(30) Foreign Application Priority Data

Jan. 22, 2003   (JP) ............................. 2003-013952

(51) Int. Cl.
*A61M 25/00* (2006.01)
(52) U.S. Cl. ....................... 604/524; 604/131
(58) Field of Classification Search ................. 604/43, 604/128, 523, 524, 528, 131
See application file for complete search history.

(56) References Cited

U.S. PATENT DOCUMENTS

| | | | | |
|---|---|---|---|---|
| 2,716,983 A | * | 9/1955 | Ryan et al. ................. 604/274 |
| 3,955,579 A | * | 5/1976 | Bridgman .................... 604/128 |
| 4,451,252 A | * | 5/1984 | Martin ......................... 604/43 |
| 5,084,013 A | * | 1/1992 | Takase ......................... 604/43 |
| 5,827,229 A |   | 10/1998 | Auth et al. .................. 604/171 |
| 5,938,645 A |   | 8/1999 | Gordon ....................... 604/264 |
| 6,152,909 A | * | 11/2000 | Bagaoisan et al. .......... 604/523 |
| 6,375,651 B2 | * | 4/2002 | Grasso et al. ................. 606/15 |
| 2006/0276774 A1 | * | 12/2006 | Mori ........................... 604/540 |

FOREIGN PATENT DOCUMENTS

| | | |
|---|---|---|
| EP | 0 570 102 A1 | 11/1993 |
| JP | 61-68035 A | 4/1986 |
| JP | 10-99428 A | 4/1998 |
| WO | 02/083229 A2 | 10/2002 |

* cited by examiner

*Primary Examiner*—Kevin C. Sirmons
*Assistant Examiner*—Andrew Gilbert
(74) *Attorney, Agent, or Firm*—Kubovcik & Kubovcik

(57) ABSTRACT

A thrombus suction catheter which is a tube having a distal end opening formed by an angled cut surface. In the distal end opening, at least a part on the proximal end side of the cut surface is formed in a concave shape in an angled direction, and the distal end side of the cut surface is formed to be flat and flexible. With the distal end configuration, suction and crossing are significantly improved.

10 Claims, 11 Drawing Sheets

THROMBUS SUCTION CATHETER WITH IMPROVED SUCTION AND CROSSING

FIELD OF THE INVENTION

The present invention relates to a thrombus suction catheter for removing a thrombus from coronary arteries, which is capable of removing atheroma by suction and has remarkably improved suction and crossing (reaching ability and smooth passage to a subject site).

BACKGROUND OF THE INVENTION

Acute myocardial infarction is a disease in which the blood vessel (coronary artery) for supplying oxygen and nutrients to the heart itself is clogged with a formed thrombus, and blood flow is blocked decreasing the function of the heart. About 40,000 people per year receive treatment for this disease in Japan. Heart disease is the first leading cause of death in Europe and the United States, and is the second leading cause of death following malignant neoplasma (cancer) in Japan, and is on the rise recently due to factors such as westernization of dietary culture and an increase in stress in social life. In recent years, treatment involving reopening of a clogged portion to allow the blood to be reperfused has been conducted, whereby the death rate in hospitals has become 10% or less. In general, as a reperfusion treatment, there are a method of injecting a drug for dissolving a thrombus and a method of expanding a blood vessel narrowed with a thrombus using a PTCA balloon catheter or the like.

It is considered that the cause of a thrombus inside the coronary arteries is as follows: a gap is formed between cells of an inner membrane (vascular endothelium) constituting the blood vessel due to stress, westernization of diet, smoking, drinking, etc.; and a low-density lipoprotein (LDL) is infiltrated through the gap. The infiltrated LDL is oxidized to become oxidized LDL. The body attempts to treat the oxidized LDL, which is a foreign matter, and macrophages gather, whereby endocytosis starts. As a result, a gruel-like substance called lipid core is accumulated between the vascular endothelium and the vascular tunica media and is expanded in a dome shape inside the blood vessel to form atheroma (see FIG. 10). When the lipid core is accumulated exceeding a certain acceptable range, the vascular endothelium in the atheroma portion ruptures. At this time, blood platelets in the blood attempt to repair the rupture portion forming a thrombus. When the thrombus is formed, blood flow in the coronary arteries is blocked. As a result, oxygen and nutrients are not supplied to the heart itself, whereby the function of the heart is lost. If the thrombus thus formed is not removed early for reperfusion, death can result.

Thrombus suction therapy is a therapeutic method of inserting a tubule with a diameter of about 1.5 mm (referred to as a catheter) through a leg or arm to allow the catheter to reach a lesion portion in the coronary arteries, and removing a thrombus itself by suction. According to the thrombus suction therapy, a thrombus causing the blood vessel to be narrowed is itself removed. Therefore, risks involved in conventional methods such as renarrowing of coronary arteries due to a thrombus that is not completely dissolved by a drug and damage caused by excess expansion of a blood vessel, can be avoided.

The above-mentioned catheter for removing a thrombus from inside the coronary arteries is called a thrombus suction catheter, which is used in combination with a suction device. The suction device conventionally includes two kinds: (1) a vacuum pump using a driving force such as electricity, and (2) a syringe. With the vacuum pump, there is a limit to the ability of a pump and a negative pressure maintenance mechanism using a check valve. Up to now, the proximal end of a catheter can produce only 640 mmHg of negative pressure.

Also, a certain degree of strength is required in a catheter so that the wall surface of the catheter is not crushed due to the negative pressure. Furthermore, in order to facilitate a discharge of an aspirated substance from a lesion portion to the outside of a body, it is necessary to maximize the area (opening area) of an opening cross-section. In a conventional catheter, the opening area remains about 0.65 $mm^2$, and the wall thickness for maintaining the strength is 0.15 mm or more. However, if the wall thickness is increased so as to avoid crushing, flexibility of the catheter is impaired. Therefore, in the case where a lesion portion is at a position that is sharply curved (e.g., #3, #4 of the coronary arteries), crossing of the catheter is unsatisfactory, making it impossible to allow the catheter to reach the lesion portion.

The shape of a distal end opening of a catheter is also important for the thrombus suction catheter.

The opening of a conventional thrombus suction catheter is angled about 30° to 45° with respect to a longitudinal axis. However, in the case where the vascular endothelium is expanded in a dome shape due to lipid core as described above, when the distal end of the catheter is cut straight, the surface of a lesion portion cannot be completely covered even if a cut surface is angled with respect to the longitudinal axis of the catheter. Thus, a gap is formed between the expanded lesion portion and the catheter. As a result, the blood flows into the catheter from the distal end of the catheter during suction, and the negative pressure produced by a suction tool cannot be completely transmitted to the lesion portion, i.e., a thrombus or the vascular endothelium of the lesion portion. Thus, sufficient suction cannot be obtained.

The present invention has been made in view of the above, and its object is to provide a thrombus suction catheter with improved suction and crossing, capable of aspirating atheroma and reaching even a lesion portion that is sharply bent.

SUMMARY OF THE INVENTION

In order to attain the above-mentioned object, the inventors of the present invention studied earnestly. As a result, the following has been found: by forming a distal end opening so that at least a part of the proximal end side of the opening is concave and the distal end side flat, crossing is improved, a lesion portion expanded at the distal end opening can be covered, and suction is remarkably improved, thereby achieving the present invention. That is, according to the present invention, there is provided a thrombus suction catheter with improved suction and crossing having a small pressure loss, which is a tube having a lumen passing through from a proximal end to a distal end, a distal end opening having an angled cut surface, in which at least a part on the proximal end side of the angled surface is formed in a concave shape in the angled direction and the distal end side of the cut surface is formed to be flat and flexible and is terminated in a necked-down tip.

Here, the distal end of the distal end opening can be eccentric to the longitudinal axis. Further, it is preferable that the pressure loss at the start of suction in the distal end opening of the catheter is 90% or less. It is preferable that the catheter is reinforced with a reinforcing wire. It is preferable that a guide wire insertion port is provided at a position 25 to 35 cm from the distal end of the distal end opening on the same side of the catheter as the reinforcing wire. Further, a marker for identifying an insertion position may be provided in a vicinity of the distal end opening.

The thrombus suction catheter of the present invention provides a further effect by combining with a suction pump. That is, the invention also relates to a thrombus suction system including suction pump and the thrombus suction catheter, in which suction pressure at the proximal end of the thrombus suction catheter is variable, and the suction is obtained continuously. Here, a suction pump which can produce a suction pressure of 650 mmHg or higher at the proximal end of the thrombus suction catheter, is preferable.

THE MOST PREFERRED EMBODIMENTS OF THE INVENTION

Next, the present invention will be described by way of examples with reference to the drawings.

Figure 1:
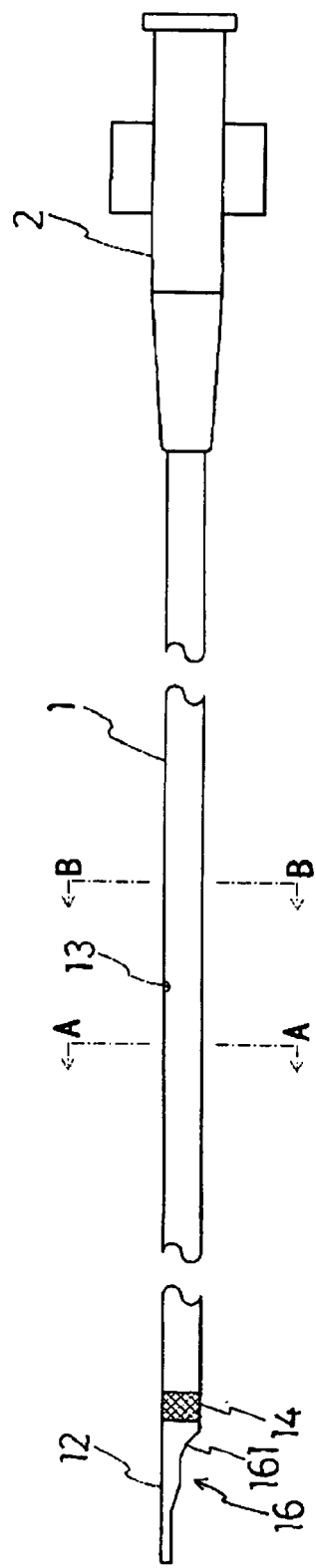
FIG. 1 is a front view of a thrombus suction catheter showing an example of the present invention.
Figure 12:
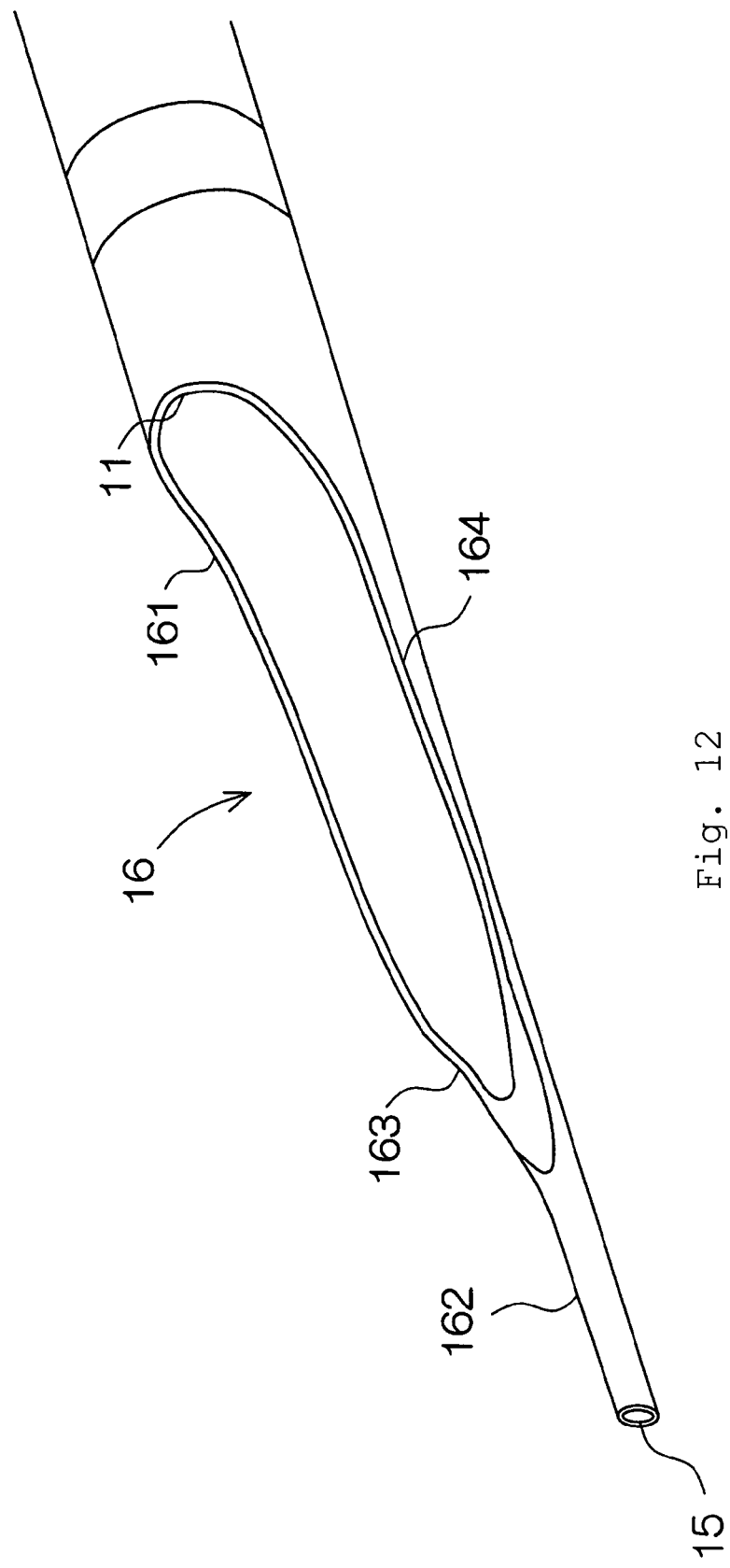
FIG. 12 is a perspective view of the catheter of the present invention.

As illustrated in FIGS. 1 and 12, a thrombus suction catheter of the present invention is a tube having a distal end opening 12 formed by an angled cut surface. In the distal end opening 12, at least a part 161 on the proximal end side of the cut surface 16 is formed in a concave shape in the angled direction, and the distal end side 163, 164 of the cut surface 16 is formed to be flat and flexible and to neck down at its tip 162. With this distal end configuration, suction and crossing are significantly improved.

Figure 2:
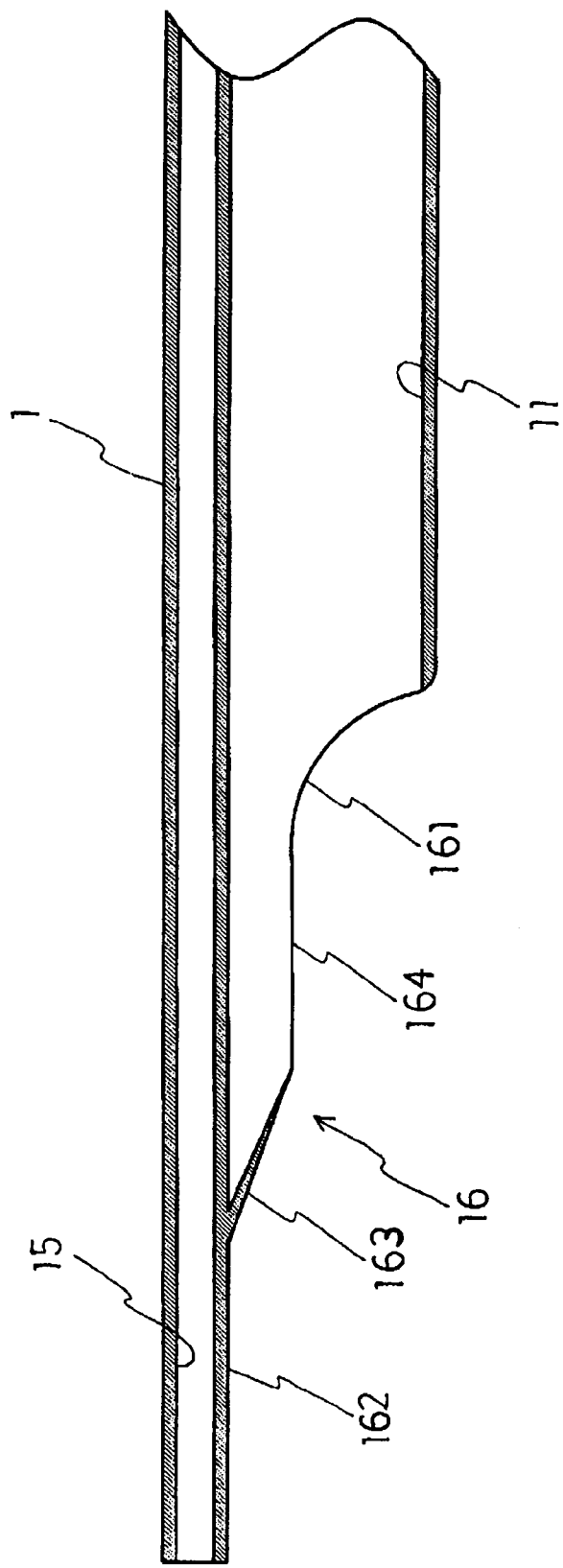
FIG. 2 is a cross-sectional view showing an enlarged main portion of FIG. 1.
Figure 3:
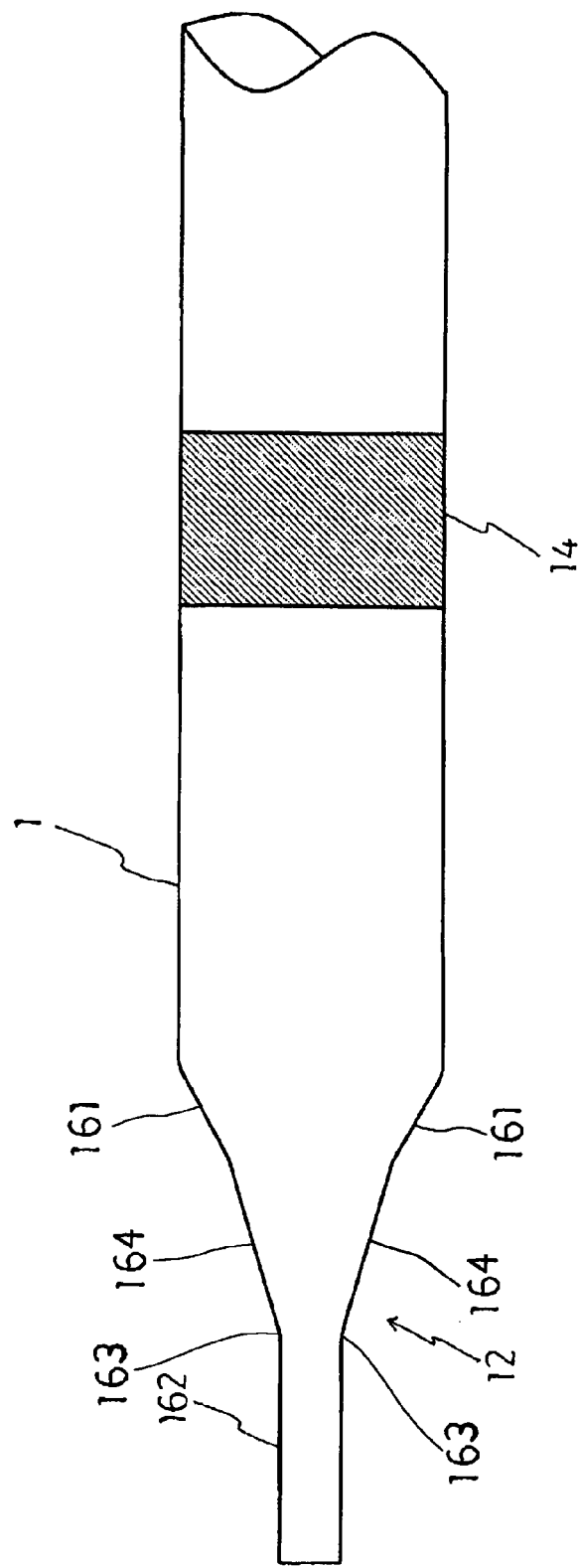
FIG. 3 is a plan view showing the enlarged main portion of FIG. 1.
Figure 4:
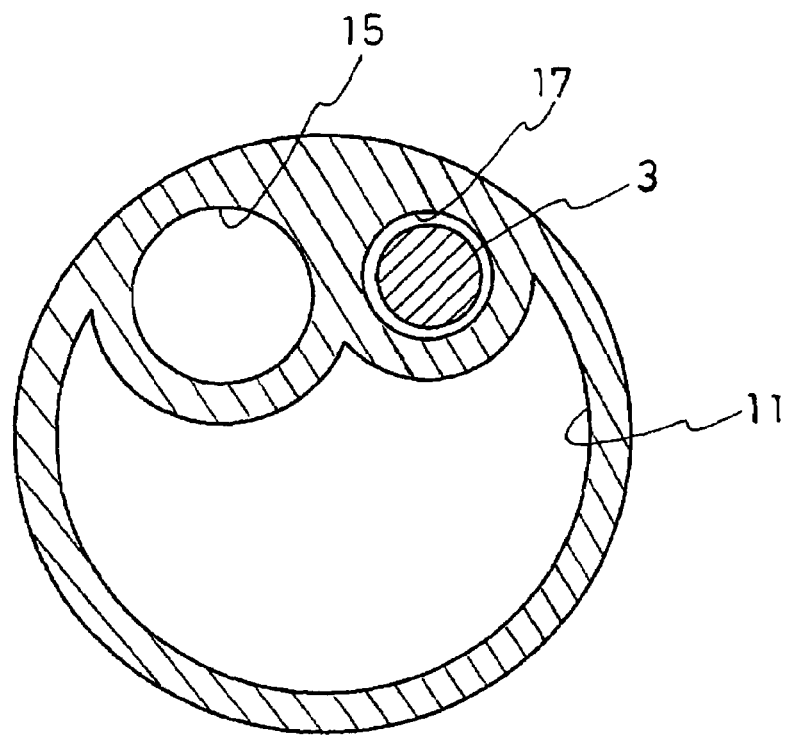
FIG. 4 is an enlarged cross-sectional view taken along line A-A shown in FIG. 1.
Figure 5:
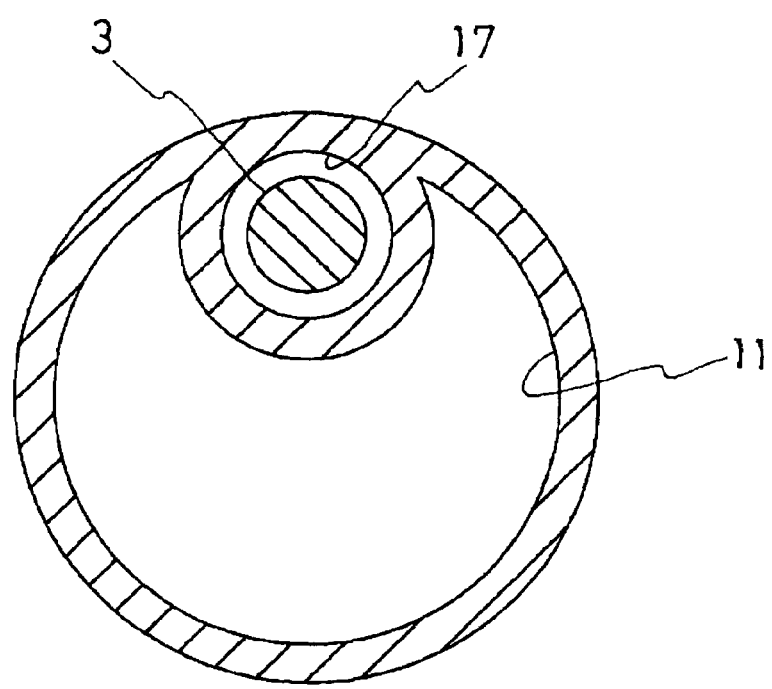
FIG. 5 is an enlarged cross-sectional view taken along line B-B shown in FIG. 1.
Figure 10:
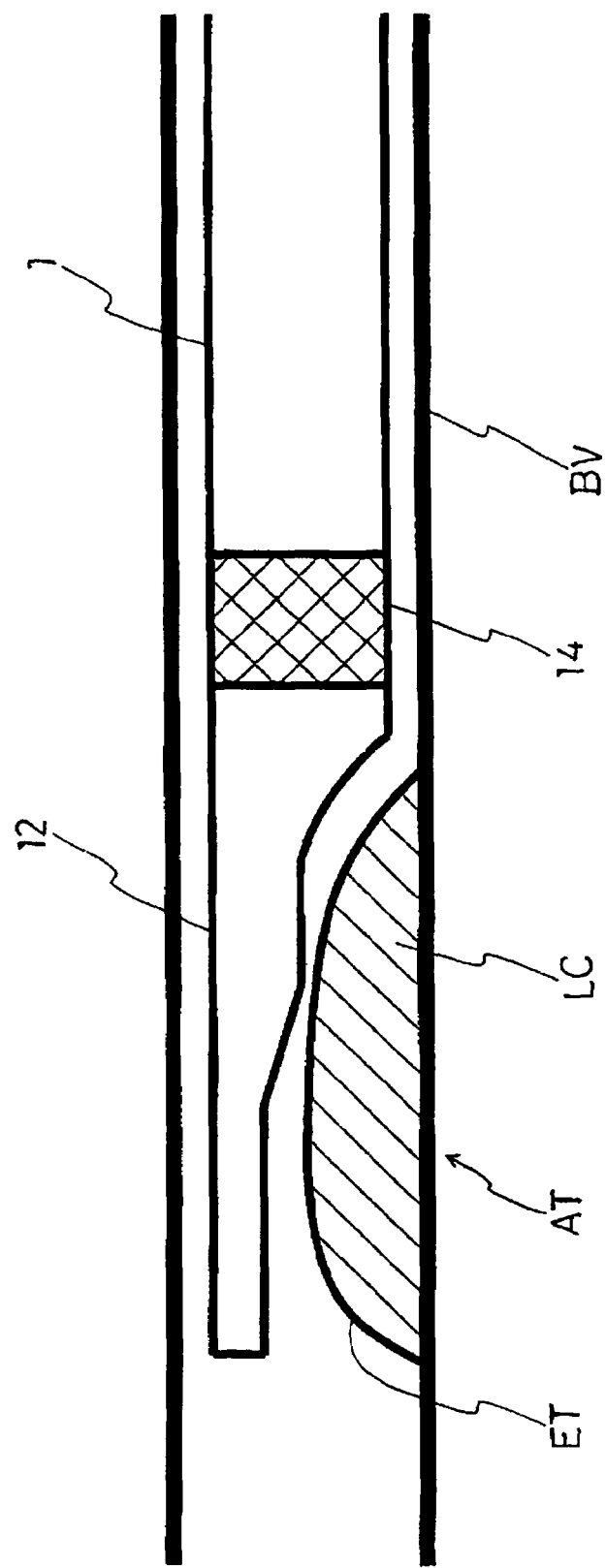
FIG. 10 is view showing a state where the thrombus suction catheter of the present invention covers an atheroma.
Figure 11:
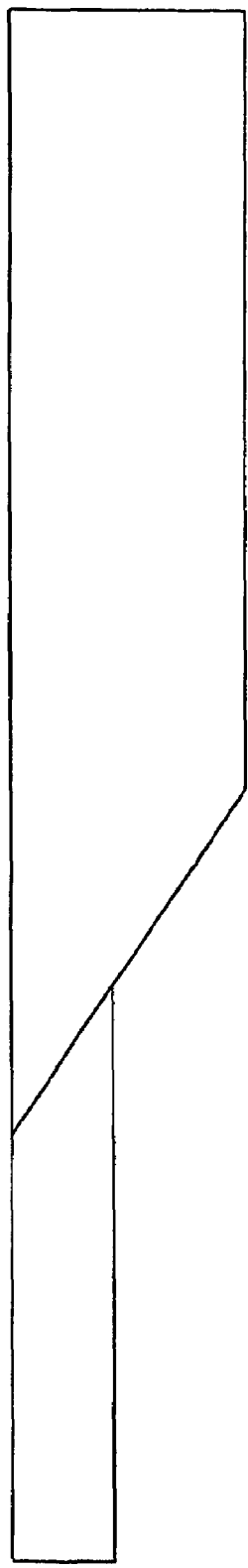
FIG. 11 is a view showing a conventional example of a thrombus suction catheter.

As shown in FIGS. 1, 4, 5 and 12, a preferred embodiment of the thrombus suction catheter includes a catheter body 1, a connector 2 provided at a proximal end of the catheter body 1, and a reinforcement wire 3 embedded in a reinforcement wire lumen 17 of the catheter body 1. The catheter body 1 is a tube formed of a flexible plastic such as polyamide elastomer, polyurethane, polyester elastomer, and polyethylene. The catheter body 1 has a lumen 11 passing through from the proximal end to a distal end, and a distal end opening 12 is provided as a thrombus suction port at the distal end. As shown in FIGS. 2 and 3, the distal end opening 12 is provided with a cut surface 16 having on its proximal end side a first cut surface 163 defining an angle with the longitudinal axis of the catheter, a rearwardly extending (in the proximal direction) ledge surface 164 parallel to the longitudinal axis of the catheter and a second concave cut surface 161 beginning at the trailing end of the ledge surface 164 and also angled with respect to the longitudinal axis. The cut surface 161 is formed in a concave shape (including the shape of an asymptote) in the angled direction as shown in FIG. 2. The concave portion 161 is a means for improving flexibility of the catheter distal end and enabling the cut surface 16 to adsorb an expanded atheroma AT by suction, when the atheroma AT as shown in FIG. 10 is covered with the distal end opening 12 and is aspirated with a suction pump (6 in FIG. 7). This remarkably enhances suction (the suction pressure becomes substantially equal to actual pump pressure when the cut surface 16 completely adsorbs the atheroma AT), and enables suction of the lipid core (LC) in a vascular endothelium (ET). Thus, the concave cut surface or portion 161 may have any shape, as long as it is angled in an angled direction, i.e., a proximal direction. Generally, the concave cut portion 161 is formed so as to be gently concave so that atheroma can be covered and the gap minimized. The concave cut portion 161 is provided at least partially on the proximal end side of the cut surface 16. More specifically, the concave portion 161 may be provided entirely on the proximal end side of the cut surface 16 (i.e., without cut surface 163 and ledge surface 164) or partially on the proximal end side (as shown, for example, in FIG. 2), considering the shape of atheroma.

The portions 163, 164 on the distal end side of the cut surface comprise means for enhancing the crossing as well as the flexibility of a catheter distal end and include a lumen 15 for a guide wire.

Figure 6:
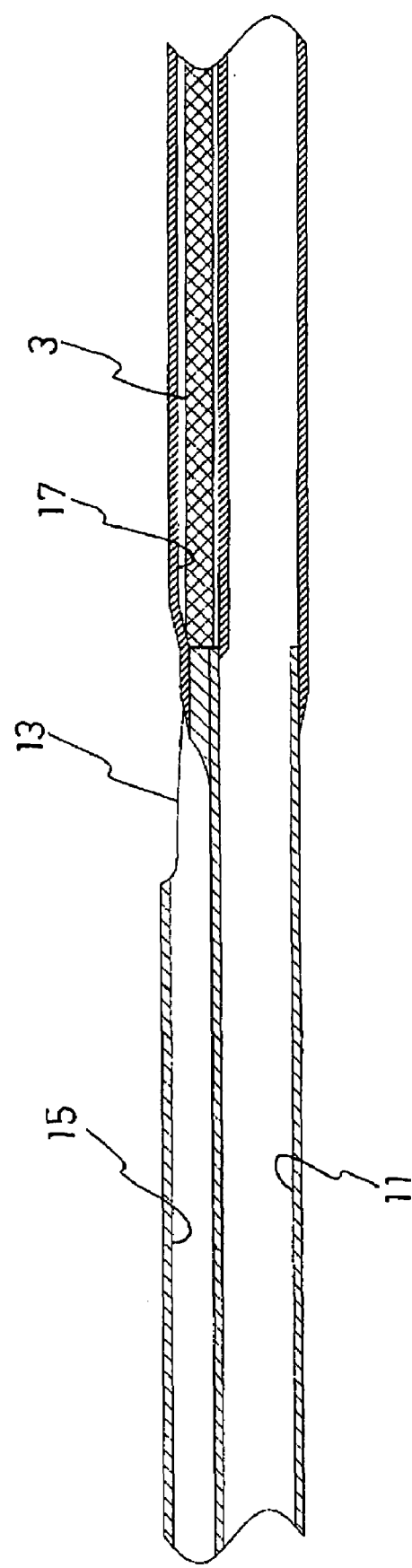
FIG. 6 a view illustrating the vicinity of a guide wire insertion port of the thrombus suction catheter shown in FIG. 1.

The lumen 11 is a path for a thrombus aspirated from the distal end opening 12, and the thrombus is collected in a thrombus collection bottle (5 in FIG. 7) through the lumen 11. The distal end side of the thrombus suction catheter is provided with guide wire lumen 15 that is opened at the distal end 162 of the catheter. Generally, a guide wire insertion port 13 is provided at a position of 2 to 50 cm from the distal end, preferably 25 to 35 cm from the distal end. Furthermore, the thrombus suction catheter is provided with a reinforcement wire lumen 17 so as to improve the ability (referred to as "pushability") of transmitting a force propelling the catheter to the distal end. A reinforcement wire 3 formed of, for example, stainless steel is embedded in the reinforcement wire lumen 17. The reinforcement wire lumen 17 extends from the proximal end of the catheter body 1 to a position of about 10 to 11 cm on the distal end side, beyond the position of the guide wire insertion port 13, and is shifted at the position of the guide wire insertion port 13 with a diameter thereof being narrowed (see FIGS. 4, 5, and 6). The reinforcement wire 3 has its distal end side tapered from the guide wire insertion port 13 in accordance with the diameter of the reinforcement wire lumen 17.

In the thrombus suction catheter of the present invention, it is preferable to provide a marker (contrast marker) 14 for identifying the insertion position of the catheter in the catheter body 1 in the vicinity of the distal end opening 12. The contrast marker 14 can be attached to the catheter body 1, for example, by caulking and wrapping a ring of platiniridium around the contrast marker 14.

In the thrombus suction catheter of the present invention, the outer wall of the catheter and the tube wall areas required for forming the guide wire lumen 15 and the reinforcement wire lumen 17 are minimized (however, the thrombus suction catheter is reinforced with the reinforcement wire 3). Therefore, the cross-sectional area of the lumen 11 is large, and pressure loss is small as will be understood from Table 1 described later.

[Crossing Test]

Figure 8:
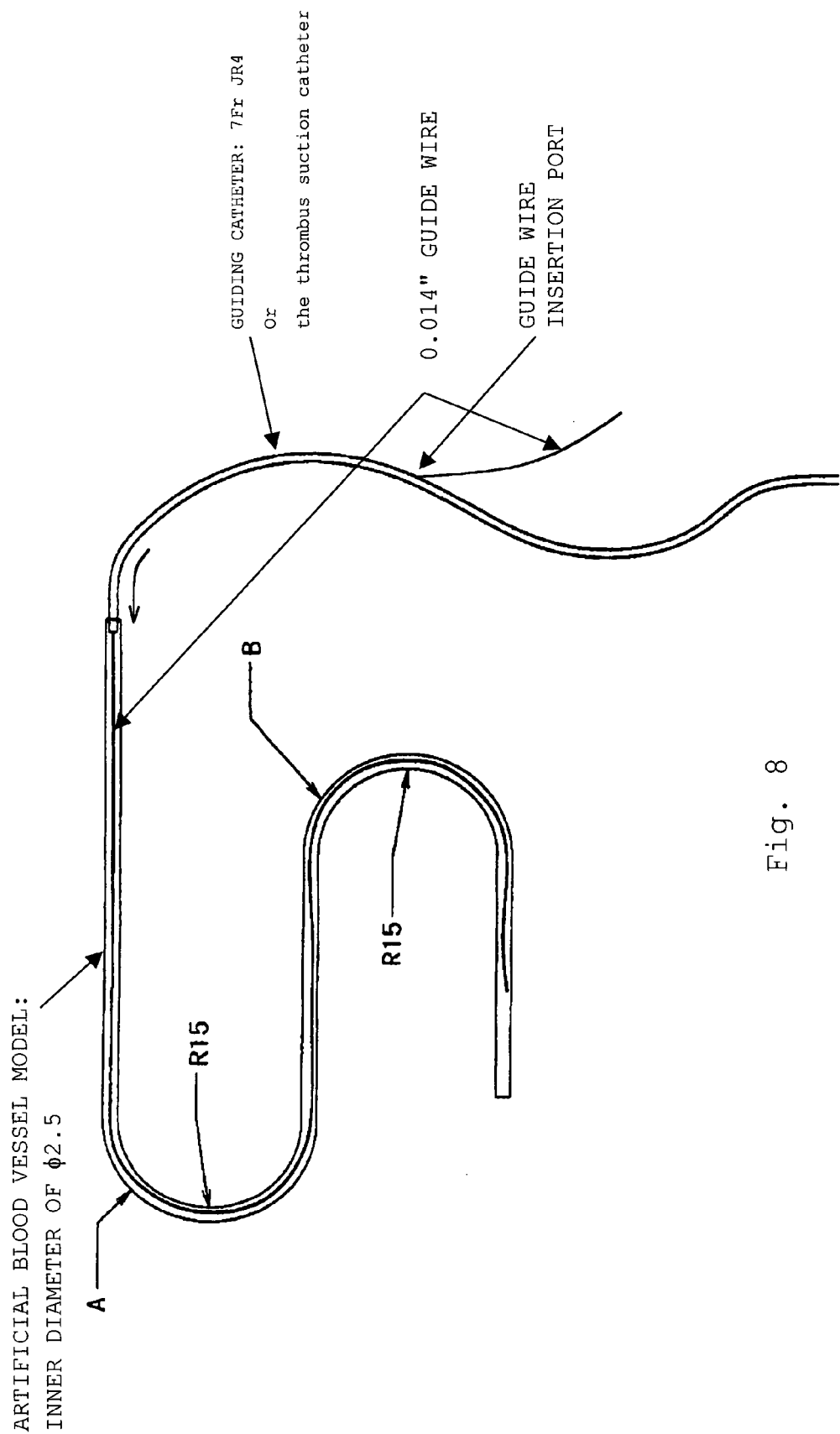
FIG. 8 is a view illustrating a crossing test.

An artificial blood vessel model and a guiding catheter (produced by Terumo Corporation, 7Fr JR4: inner diameter 0.075∝) lightly attached to the model as shown in FIG. 8 were prepared. The artificial blood vessel model (wave type with a length of 200 mm, an inner diameter of 3 mm, and a cycle of 20 mm) was immersed in hot water at 37° C., and a guide wire (produced by ACS, HI-TORQUE BALANCE MIDDLEWEIGHT, 0.014") was inserted into the model. After that, the thrombus suction catheter was moved forward along the guide wire, and an insertion length of the catheter when the artificial blood vessel model was separated from the guiding catheter was recorded. A thrombus suction catheter (N=10) of the present invention reached a position B (insertion length: 17 cm), whereas a commercially available thrombus suction catheter (N=2, produced by S company, a distal end thereof is diagonally cut in a straight line) only reached a position A (insertion length: 9 cm). The thrombus suction catheter of the example had an outer diameter of 4.5 Fr (corresponding to an outer diameter of 1.43 mm), and a lumen cross-sectional area of 0.90 $mm^2$ on the proximal end side and 0.80 $mm^2$ on the distal end side from the guide wire insertion port. The thrombus suction catheter of the comparative example had an outer diameter of 4.5 Fr, and a lumen cross-sectional area of 0.65 $mm^2$.

As a result, it is understood that crossing of the thrombus suction catheter of the present invention was remarkably improved, compared with that of the commercially available thrombus suction catheter.

[Suction Pressure Comparison Test]

Figure 9:
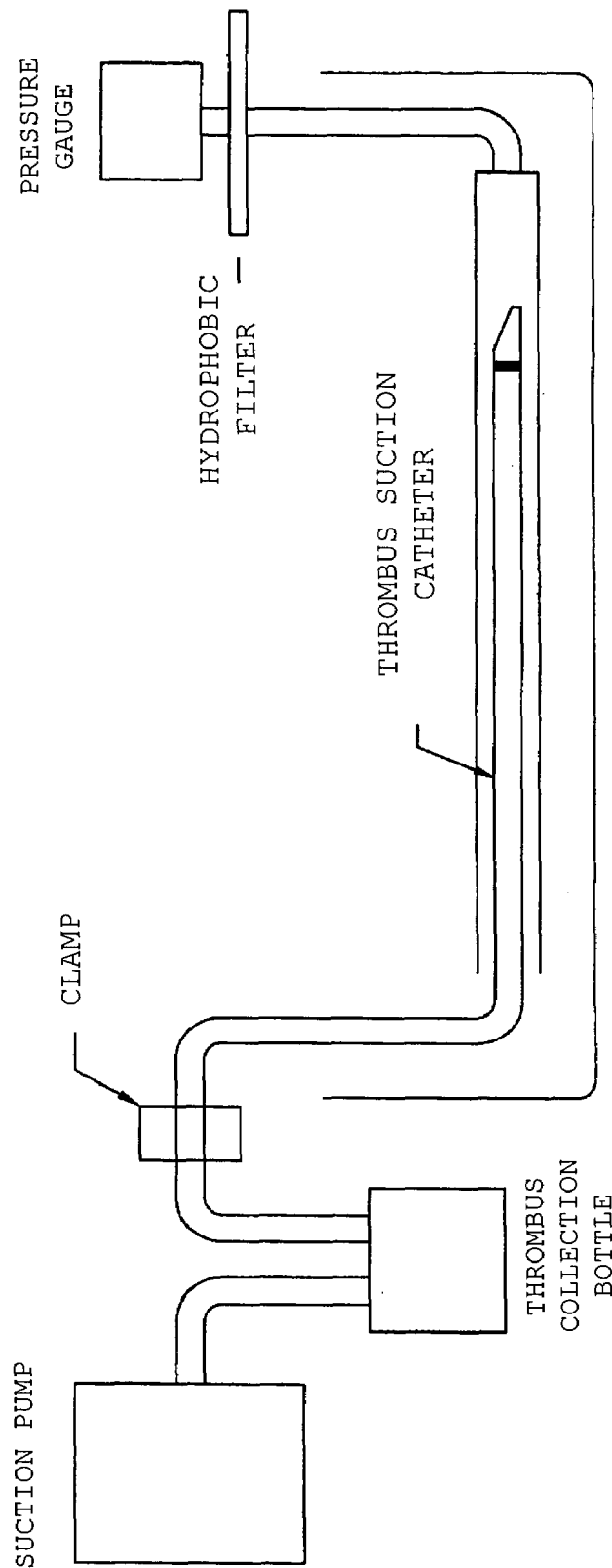
FIG. 9 is a view illustrating a suction pressure comparison test.

Water was added to glycerin to obtain a preparatory liquid 5 with substantially the same viscosity as that of blood. As shown in FIG. 9, a thrombus suction catheter (Example, N=10) of the present invention similar to that used in the crossing test and the above-mentioned commercially available catheter (Comparative Example, N=5) were used. The catheters were respectively inserted into elongated tubes with an outer diameter of 2.5 mm, and immersed in the preparatory liquid. The suction pressure was measured with a varying pressure of a pump and a varying distance from a pressure gauge. The results as shown in Table 1 were obtained. The sealing position in a suction pressure measurement system was set to be the position of a hydrophobic filter.

It is understood from the table that the suction force of the catheter of the present invention is about twice that of the commercially available thrombus suction catheter, and the pressure loss at the start of suction at the distal end opening is 90% or less.

TABLE 1

| | Set pressure (mmHg) | Actual pump pressure (mmHg) | Suction pressure | | |
|---|---|---|---|---|---|
| | | | 0 mm*1 | 60 mm*2 | 100 mm*3 |
| Example 1 | 600 | 596 | 63 | 60 | 58.5 |
| Example 2 | 640 | 637 | 69 | 69 | 61.5 |
| Example 3 | 680 | 679 | 81 | 75 | 72 |
| Example 4 | 700 | 699 | 79.5 | 76.5 | 81 |
| Comparative Example 1 | 600 | 596 | 36 | 34.5 | 34.5 |
| Comparative Example 2 | 640 | 637 | 37.5 | 37.5 | 33 |
| Comparative Example 3 | 680 | 679 | 39 | 37.5 | 30 |
| Comparative Example 4 | 700 | 699 | 42 | 39 | 30 |

*1, *2, *3: distance between the thrombus suction catheter and the connecting portion to the tube of the pressure gauge.

Next, a thrombus suction system of the present invention will be described.

Figure 7:
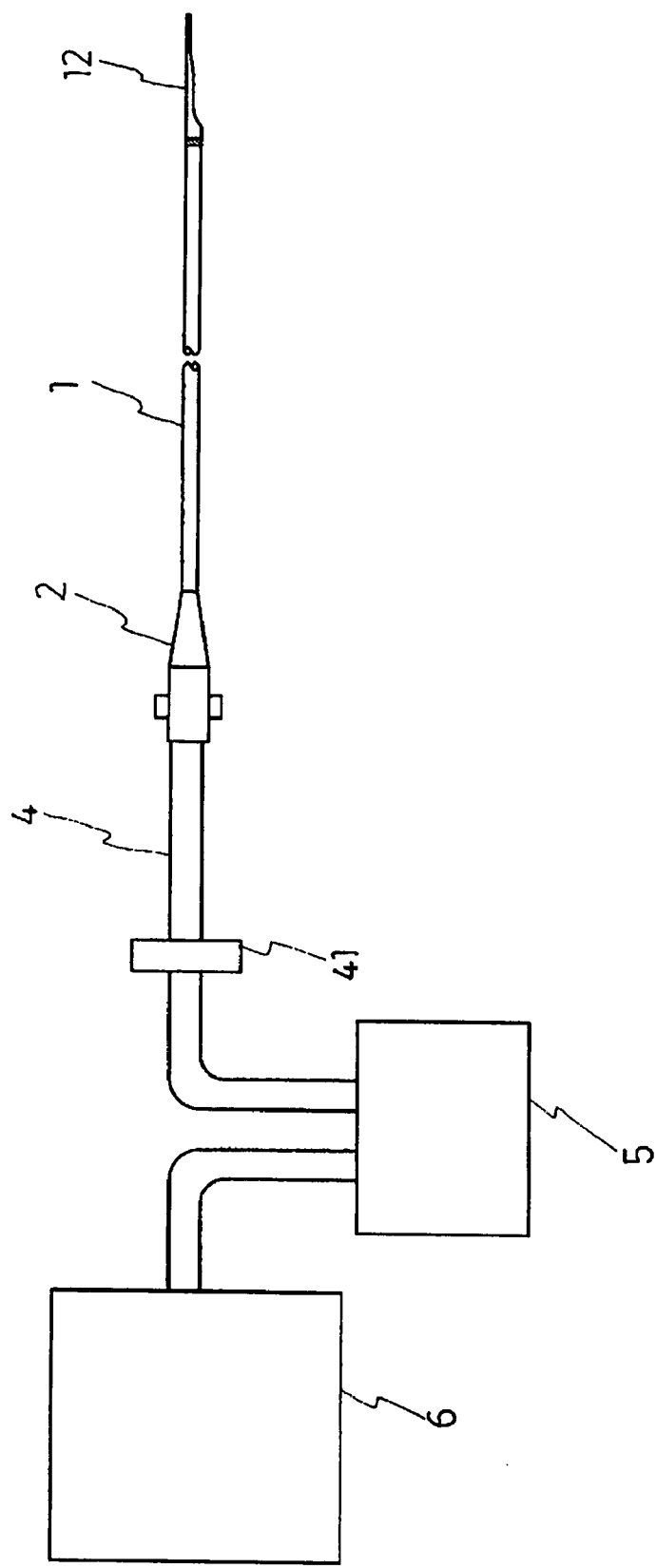
FIG. 7 is a view illustrating a thrombus suction system of the present invention.

The thrombus suction system includes the thrombus suction catheter of the present invention and a suction pump 6, as shown in FIG. 7, and is generally combined with an extension tube 4 and a thrombus collection bottle 5. The extension tube 4 is provided with a clamp 41, and the clamp 41 is closed before and after the thrombus suction. When the clamp 41 is opened to drive the suction pump 6, the suction of a thrombus is started. The thrombus aspirated from the distal end opening 12 is collected in the thrombus collection bottle 5 through the catheter body 1 and the extension tube 4.

As the suction pump 6 useful in the present invention, those which can produce a suction pressure of 650 mmHg or higher at the proximal end (proximal end of the connector 2) of the thrombus suction catheter can be used.

According to the present invention, the suction pump 6 is used as suction means. Therefore, the suction pressure at the proximal end of the thrombus suction catheter can be varied arbitrarily in accordance with a lesion. Furthermore, the suction pressure can be obtained continuously, so that treatment can be performed in a short period of time.

INDUSTRIAL APPLICABILITY

As is apparent from the above description, the thrombus suction catheter of the present invention has a crossing that enables the catheter to reach even a lesion portion sharply bent. Therefore, the catheter can reach even a portion sharply curved, such as #3 and #4 of the coronary arteries, which were impossible to reach conventionally. Furthermore, the thrombus suction catheter of the present invention has a large cross-sectional area of a lumen and has strength of such magnitude that the catheter withstands a suction force of 650 mmHg or higher. Therefore, the thrombus suction catheter of the present invention has a large suction force at the distal end opening and is excellent in thrombus removal ability. Still furthermore, the distal end opening is of a shape such that the opening is likely to adsorb a atheroma during suction. Therefore, a large suction force can be obtained, and atheroma can be aspirated.

What is claimed is:

1. A thrombus suction catheter comprising a flexible plastic tube having a first lumen passing through from a proximal end to a distal end of the catheter, an opening at the distal end of the catheter, an insertion port for a guidewire provided in the catheter at a position apart from the distal end of the catheter, and a second lumen provided for the guidewire and extending from the insertion port to the opening at the distal end of the catheter, wherein the opening at the distal end of the catheter comprises a cut surface angled with respect to the axis of the catheter, the cut surface terminating in a necked-down tip in an axial direction at a distal side of the cut surface, and the necked-down tip including the second lumen provided for the guidewire, and the cut surface including a first cut surface extending from a proximal side of the neck-down tip and angled in the proximal direction of the catheter, a ledge surface which is substantially parallel to the longitudinal axis of the catheter and extends from the first cut surface in the proximal direction and a second concave cut surface extending from the ledge surface and angled in the proximal direction of the catheter;

whereby the thrombus catheter is provided with improved suction, reaching ability and passage in a body to a lesion portion in a coronary artery.

2. The thrombus suction catheter according to claim 1, wherein the necked-down tip is eccentric to the longitudinal axis of the catheter.

3. The thrombus suction catheter according to claim 1, wherein the opening at the distal end of the catheter provides a pressure loss at a start of suction of 90% or less.

4. The thrombus suction catheter according to claim 1, wherein the insertion port for the guide wire is provided at a position 25 to 35 cm from the distal end of the opening at the distal end of the catheter.

5. The thrombus suction catheter according to claim 2, wherein the insertion port for the guide wire is provided at a position 25 to 35 cm from the distal end of the opening at the distal end of the catheter.

6. The thrombus suction catheter according to claim 1, wherein a marker for identifying a position of the catheter is provided in a vicinity of the distal end opening.

7. A thrombus suction system comprising a suction pump and the thrombus suction catheter of claim 1, wherein the suction pump provides a variable and continuous pressure at the proximal end of the thrombus suction catheter.

8. The thrombus suction system according to claim 7, wherein the suction pump is capable of producing a suction pressure of 650 mmHg or higher at the proximal end of the thrombus suction catheter.

9. A thrombus suction catheter according to claim 1, further comprising a third lumen provided for a reinforcing wire and extending from the proximal end of the catheter to a position beyond said insertion port and to a position apart from the distal end of the catheter.

10. The throinbus suction catheter according to claim 9, further comprising a reinforcing wire in said third lumen.

* * * * *